(12) United States Patent
Ghaffari et al.

(10) Patent No.: US 9,833,190 B2
(45) Date of Patent: Dec. 5, 2017

(54) METHODS OF DETECTING PARAMETERS OF A LUMEN

(71) Applicant: MC10, Inc., Lexington, MA (US)

(72) Inventors: Roozbeh Ghaffari, Cambridge, MA (US); Gilman Callsen, Malden, MA (US); William J. Arora, Bellevue, WA (US); Benjamin Schlatka, Lexington, MA (US)

(73) Assignee: MC10, Inc., Lexington, MA (US)

( * ) Notice: Subject to any disclaimer, the term of this patent is extended or adjusted under 35 U.S.C. 154(b) by 0 days.

(21) Appl. No.: 15/003,644

(22) Filed: Jan. 21, 2016

(65) Prior Publication Data

US 2016/0135740 A1    May 19, 2016

Related U.S. Application Data

(62) Division of application No. 12/575,008, filed on Oct. 7, 2009, now Pat. No. 9,289,132.

(Continued)

(51) Int. Cl.
*A61B 5/01* (2006.01)
*A61B 1/00* (2006.01)
(Continued)

(52) U.S. Cl.
CPC ........ *A61B 5/4836* (2013.01); *A61B 1/00082* (2013.01); *A61B 1/3137* (2013.01); *A61B 5/01* (2013.01); *A61B 5/015* (2013.01); *A61B 5/02007* (2013.01); *A61B 5/02014* (2013.01); *A61B 5/0536* (2013.01); *A61B 5/6853* (2013.01); *A61B 5/7271* (2013.01);
(Continued)

(58) Field of Classification Search
CPC . A61B 5/4836; A61B 5/7271; A61B 5/02007; A61B 5/02014; A61B 5/015; A61B 5/6853; A61M 2025/1086; A61M 25/10
See application file for complete search history.

(56) References Cited

U.S. PATENT DOCUMENTS 3,716,861 A    2/1973 Root
3,805,427 A    4/1974 Epstein
(Continued)

FOREIGN PATENT DOCUMENTS

EP    0585670 A2    3/1994
EP    0779059 A1    6/1997
(Continued)

OTHER PUBLICATIONS

Carvalhal et al., "Electrochemical Detection in a Paper-Based Separation Device", Analytical Chemistry, vol. 82, No. 3, (1162-1165) (4 pages) (Jan. 7, 2010).
(Continued)

*Primary Examiner* — Nathan R Price
*Assistant Examiner* — Weng Lee
(74) *Attorney, Agent, or Firm* — Nixon Peabody LLP

(57) ABSTRACT

A system, device and method are presented for utilizing stretchable active integrated circuits with inflatable bodies. The invention allows for such operative features to come into direct contact with body structures, such as the inner wall of a lumen. Such direct contact increases accuracy of measurement and delivery of therapy.

29 Claims, 4 Drawing Sheets

Related U.S. Application Data

(60) Provisional application No. 61/103,361, filed on Oct. 7, 2008, provisional application No. 61/113,007, filed on Nov. 10, 2008.

(51) Int. Cl.

| | |
|---|---|
| *A61B 5/02* | (2006.01) |
| *A61B 5/00* | (2006.01) |
| *A61B 5/053* | (2006.01) |
| *A61B 1/313* | (2006.01) |
| *A61M 25/10* | (2013.01) |
| *A61F 2/958* | (2013.01) |

(52) U.S. Cl.
CPC .............. *A61M 25/10* (2013.01); *A61F 2/958* (2013.01); *A61M 2025/1086* (2013.01)

(56) References Cited

U.S. PATENT DOCUMENTS

| | | | |
|---|---|---|---|
| 4,304,235 | A | 12/1981 | Kaufman |
| 4,416,288 | A | 11/1983 | Freeman |
| 4,658,153 | A | 4/1987 | Brosh |
| 5,272,375 | A | 12/1993 | Belopolsky |
| 5,306,917 | A | 4/1994 | Black |
| 5,326,521 | A | 7/1994 | East |
| 5,331,966 | A | 7/1994 | Bennett |
| 5,360,987 | A | 11/1994 | Shibib |
| 5,454,270 | A | 10/1995 | Brown |
| 5,471,982 | A | 12/1995 | Edwards |
| 5,491,651 | A | 2/1996 | Janic |
| 5,549,108 | A | 8/1996 | Edwards |
| 5,567,975 | A | 10/1996 | Walsh |
| 5,580,794 | A | 12/1996 | Allen |
| 5,617,870 | A | 4/1997 | Hastings |
| 5,674,198 | A | 10/1997 | Leone |
| 5,811,790 | A | 9/1998 | Endo |
| 5,817,008 | A | 10/1998 | Rafert |
| 5,907,477 | A | 5/1999 | Tuttle |
| 6,063,046 | A | 5/2000 | Allum |
| 6,265,090 | B1 | 7/2001 | Nishide |
| 6,282,960 | B1 | 9/2001 | Samuels |
| 6,343,514 | B1 | 2/2002 | Smith |
| 6,387,052 | B1 | 5/2002 | Quinn et al. |
| 6,410,971 | B1 | 6/2002 | Otey |
| 6,421,016 | B1 | 7/2002 | Phillips |
| 6,455,931 | B1 | 9/2002 | Hamilton |
| 6,567,158 | B1 | 5/2003 | Falcial |
| 6,641,860 | B1 | 11/2003 | Kaiserman |
| 6,775,906 | B1 | 8/2004 | Silverbrook |
| 6,784,844 | B1 | 8/2004 | Boakes |
| 6,965,160 | B2 | 11/2005 | Cobbley |
| 6,987,314 | B1 | 1/2006 | Yoshida |
| 7,259,030 | B2 | 8/2007 | Daniels |
| 7,265,298 | B2 | 9/2007 | Maghribi |
| 7,302,751 | B2 | 12/2007 | Hamburgen |
| 7,337,012 | B2 | 2/2008 | Maghribi |
| 7,487,587 | B2 | 2/2009 | Vanfleteren |
| 7,491,892 | B2 | 2/2009 | Wagner |
| 7,521,292 | B2 | 4/2009 | Rogers |
| 7,557,367 | B2 | 7/2009 | Rogers |
| 7,618,260 | B2 | 11/2009 | Daniel |
| 7,622,367 | B1 | 11/2009 | Nuzzo |
| 7,727,199 | B2 | 6/2010 | Fernandes |
| 7,727,228 | B2 | 6/2010 | Abboud |
| 7,739,791 | B2 | 6/2010 | Brandenburg |
| 7,759,167 | B2 | 7/2010 | Vanfleteren |
| 7,960,246 | B2 | 6/2011 | Flamand |
| 7,982,296 | B2 | 7/2011 | Nuzzo |
| 8,097,926 | B2 | 1/2012 | De Graff et al. |
| 8,198,621 | B2 | 6/2012 | Rogers |
| 8,207,473 | B2 | 6/2012 | Axisa |
| 8,217,381 | B2 | 7/2012 | Rogers |
| 8,372,726 | B2 | 2/2013 | De Graff et al. |
| 8,389,862 | B2 | 3/2013 | Arora |
| 8,431,828 | B2 | 4/2013 | Vanfleteren |
| 8,440,546 | B2 | 5/2013 | Nuzzo |
| 8,536,667 | B2 | 9/2013 | De Graff et al. |
| 8,552,299 | B2 | 10/2013 | Rogers |
| 8,664,699 | B2 | 3/2014 | Nuzzo |
| 8,679,888 | B2 | 3/2014 | Rogers |
| 8,729,524 | B2 | 5/2014 | Rogers |
| 8,754,396 | B2 | 6/2014 | Rogers |
| 8,865,489 | B2 | 10/2014 | Rogers |
| 8,886,334 | B2 | 11/2014 | Ghaffari et al. |
| 8,905,772 | B2 | 12/2014 | Rogers |
| 9,012,784 | B2 | 4/2015 | Arora et al. |
| 9,082,025 | B2 | 7/2015 | Fastert et al. |
| 9,105,555 | B2 | 8/2015 | Rogers |
| 9,105,782 | B2 | 8/2015 | Rogers |
| 9,119,533 | B2 | 9/2015 | Ghaffari |
| 9,123,614 | B2 | 9/2015 | Graff et al. |
| 9,159,635 | B2 | 10/2015 | Elolampi et al. |
| 9,168,094 | B2 | 10/2015 | Lee et al. |
| 9,171,794 | B2 | 10/2015 | Rafferty et al. |
| 9,186,060 | B2 | 11/2015 | De Graff et al. |
| 9,226,402 | B2 | 12/2015 | Hsu |
| 9,247,637 | B2 | 1/2016 | Hsu |
| 9,289,132 | B2 | 3/2016 | Ghaffari et al. |
| 2001/0012918 | A1 | 8/2001 | Swanson |
| 2001/0021867 | A1 | 9/2001 | Kordis |
| 2002/0026127 | A1 | 2/2002 | Balbierz |
| 2002/0082515 | A1 | 6/2002 | Campbell |
| 2002/0087146 | A1 | 7/2002 | Schu |
| 2002/0094701 | A1* | 7/2002 | Biegelsen .............. B25J 13/084 439/32 |
| 2002/0113739 | A1 | 8/2002 | Howard |
| 2002/0128700 | A1 | 9/2002 | Cross, Jr. |
| 2002/0145467 | A1 | 10/2002 | Minch |
| 2002/0151934 | A1 | 10/2002 | Levine |
| 2002/0158330 | A1 | 10/2002 | Moon |
| 2003/0017848 | A1 | 1/2003 | Engstrom |
| 2003/0023287 | A1 | 1/2003 | Edwards |
| 2003/0045025 | A1 | 3/2003 | Coyle |
| 2003/0097165 | A1 | 5/2003 | Krulevitch |
| 2003/0120271 | A1 | 6/2003 | Burnside |
| 2003/0162507 | A1 | 8/2003 | Vatt |
| 2003/0214408 | A1 | 11/2003 | Grajales |
| 2003/0236455 | A1 | 12/2003 | Swanson |
| 2004/0006264 | A1 | 1/2004 | Mojarradi |
| 2004/0085469 | A1 | 5/2004 | Johnson |
| 2004/0092806 | A1 | 5/2004 | Sagon |
| 2004/0106334 | A1 | 6/2004 | Suzuki |
| 2004/0135094 | A1 | 7/2004 | Niigaki |
| 2004/0138558 | A1 | 7/2004 | Dunki-Jacobs |
| 2004/0149921 | A1 | 8/2004 | Smyk |
| 2004/0178466 | A1 | 9/2004 | Merrill |
| 2004/0192082 | A1 | 9/2004 | Wagner |
| 2004/0201134 | A1 | 10/2004 | Kawai |
| 2004/0203486 | A1 | 10/2004 | Shepherd |
| 2004/0221370 | A1 | 11/2004 | Hannula |
| 2004/0243204 | A1 | 12/2004 | Maghribi |
| 2005/0021103 | A1 | 1/2005 | DiLorenzo |
| 2005/0029680 | A1 | 2/2005 | Jung |
| 2005/0067293 | A1 | 3/2005 | Naito |
| 2005/0070778 | A1 | 3/2005 | Lackey |
| 2005/0096513 | A1 | 5/2005 | Ozguz |
| 2005/0113744 | A1 | 5/2005 | Donoghue |
| 2005/0139683 | A1 | 6/2005 | Yi |
| 2005/0171524 | A1 | 8/2005 | Stern |
| 2005/0203366 | A1 | 9/2005 | Donoghue |
| 2006/0003709 | A1 | 1/2006 | Wood |
| 2006/0038182 | A1 | 2/2006 | Rogers |
| 2006/0071349 | A1 | 4/2006 | Tokushige |
| 2006/0084394 | A1 | 4/2006 | Engstrom |
| 2006/0106321 | A1* | 5/2006 | Lewinsky .......... A61B 5/02007 600/491 |
| 2006/0128346 | A1 | 6/2006 | Yasui |
| 2006/0154398 | A1 | 7/2006 | Qing |
| 2006/0160560 | A1 | 7/2006 | Josenhans |
| 2006/0248946 | A1 | 11/2006 | Howell |
| 2006/0257945 | A1 | 11/2006 | Masters |
| 2006/0264767 | A1 | 11/2006 | Shennib |
| 2006/0270135 | A1 | 11/2006 | Chrysler |

(56) References Cited

U.S. PATENT DOCUMENTS

| | | |
|---|---|---|
| 2006/0286785 A1 | 12/2006 | Rogers |
| 2007/0016279 A1 | 1/2007 | Konstantino |
| 2007/0027514 A1* | 2/2007 | Gerber ................... A61N 1/05 607/116 |
| 2007/0031283 A1 | 2/2007 | Davis |
| 2007/0108389 A1 | 5/2007 | Makela |
| 2007/0113399 A1 | 5/2007 | Kumar |
| 2007/0123756 A1 | 5/2007 | Kitajima |
| 2007/0270672 A1 | 11/2007 | Hayter |
| 2008/0036097 A1 | 2/2008 | Ito |
| 2008/0046080 A1 | 2/2008 | Vanden Bulcke |
| 2008/0074383 A1 | 3/2008 | Dean |
| 2008/0096620 A1 | 4/2008 | Lee |
| 2008/0139894 A1 | 6/2008 | Szydlo-Moore |
| 2008/0157235 A1 | 7/2008 | Rogers |
| 2008/0188912 A1 | 8/2008 | Stone |
| 2008/0193749 A1 | 8/2008 | Thompson |
| 2008/0204021 A1 | 8/2008 | Leussler |
| 2008/0211087 A1 | 9/2008 | Mueller-Hipper |
| 2008/0237840 A1 | 10/2008 | Alcoe |
| 2008/0259576 A1 | 10/2008 | Johnson |
| 2008/0287167 A1 | 11/2008 | Caine |
| 2008/0313552 A1 | 12/2008 | Buehler |
| 2009/0000377 A1 | 1/2009 | Shipps |
| 2009/0001550 A1 | 1/2009 | Li |
| 2009/0015560 A1 | 1/2009 | Robinson |
| 2009/0017884 A1 | 1/2009 | Rotschild |
| 2009/0048556 A1 | 2/2009 | Durand |
| 2009/0088750 A1 | 4/2009 | Hushka |
| 2009/0107704 A1 | 4/2009 | Vanfleteren |
| 2009/0154736 A1 | 6/2009 | Lee |
| 2009/0184254 A1 | 7/2009 | Miura |
| 2009/0204168 A1 | 8/2009 | Kallmyer |
| 2009/0215385 A1 | 8/2009 | Waters |
| 2009/0225751 A1 | 9/2009 | Koenck |
| 2009/0261828 A1 | 10/2009 | Nordmeyer-Massner |
| 2009/0273909 A1 | 11/2009 | Shin |
| 2009/0283891 A1 | 11/2009 | Dekker |
| 2009/0291508 A1 | 11/2009 | Babu |
| 2009/0294803 A1 | 12/2009 | Nuzzo |
| 2009/0322480 A1 | 12/2009 | Benedict |
| 2010/0002402 A1 | 1/2010 | Rogers |
| 2010/0059863 A1 | 3/2010 | Rogers |
| 2010/0072577 A1 | 3/2010 | Nuzzo |
| 2010/0073669 A1 | 3/2010 | Colvin, Jr. |
| 2010/0087782 A1 | 4/2010 | Ghaffari et al. |
| 2010/0090781 A1 | 4/2010 | Yamamoto |
| 2010/0090824 A1 | 4/2010 | Rowell |
| 2010/0116526 A1 | 5/2010 | Arora et al. |
| 2010/0117660 A1 | 5/2010 | Douglas |
| 2010/0178722 A1 | 7/2010 | De Graff et al. |
| 2010/0245011 A1 | 9/2010 | Chatzopoulos |
| 2010/0271191 A1 | 10/2010 | De Graff et al. |
| 2010/0298895 A1 | 11/2010 | Ghaffari |
| 2010/0317132 A1 | 12/2010 | Rogers |
| 2010/0321161 A1 | 12/2010 | Isabell |
| 2010/0327387 A1 | 12/2010 | Kasai |
| 2011/0011179 A1 | 1/2011 | Gustafsson |
| 2011/0034912 A1 | 2/2011 | De Graff |
| 2011/0051384 A1 | 3/2011 | Kriechbaum |
| 2011/0054583 A1 | 3/2011 | Litt |
| 2011/0101789 A1 | 5/2011 | Salter, Jr. |
| 2011/0121822 A1 | 5/2011 | Parsche |
| 2011/0140897 A1 | 6/2011 | Purks |
| 2011/0175735 A1 | 7/2011 | Forster |
| 2011/0184320 A1 | 7/2011 | Shipps |
| 2011/0215931 A1 | 9/2011 | Callsen et al. |
| 2011/0218756 A1 | 9/2011 | Callsen et al. |
| 2011/0218757 A1 | 9/2011 | Callsen |
| 2011/0220890 A1 | 9/2011 | Nuzzo |
| 2011/0277813 A1 | 11/2011 | Rogers |
| 2011/0284268 A1 | 11/2011 | Palaniswamy |
| 2011/0306851 A1 | 12/2011 | Wang |
| 2012/0016258 A1 | 1/2012 | Webster |
| 2012/0051005 A1 | 3/2012 | Vanfleteren |
| 2012/0052268 A1 | 3/2012 | Axisa |
| 2012/0065937 A1 | 3/2012 | De Graff |
| 2012/0074546 A1 | 3/2012 | Chong |
| 2012/0087216 A1 | 4/2012 | Keung |
| 2012/0091594 A1 | 4/2012 | Landesberger |
| 2012/0092178 A1 | 4/2012 | Callsen |
| 2012/0092222 A1 | 4/2012 | Kato |
| 2012/0101413 A1 | 4/2012 | Beetel |
| 2012/0101538 A1 | 4/2012 | Ballakur |
| 2012/0108012 A1 | 5/2012 | Yasuda |
| 2012/0126418 A1 | 5/2012 | Feng |
| 2012/0157804 A1 | 6/2012 | Rogers |
| 2012/0172697 A1 | 7/2012 | Urman |
| 2012/0226130 A1 | 9/2012 | De Graff |
| 2012/0244848 A1 | 9/2012 | Ghaffari |
| 2012/0256308 A1 | 10/2012 | Helin |
| 2012/0316455 A1 | 12/2012 | Rahman |
| 2012/0327608 A1 | 12/2012 | Rogers |
| 2013/0041235 A1 | 2/2013 | Rogers |
| 2013/0099358 A1 | 4/2013 | Elolampi |
| 2013/0100618 A1 | 4/2013 | Rogers |
| 2013/0118255 A1 | 5/2013 | Callsen |
| 2013/0150693 A1 | 6/2013 | D'Angelo |
| 2013/0185003 A1 | 7/2013 | Carbeck |
| 2013/0192356 A1 | 8/2013 | De Graff |
| 2013/0200268 A1 | 8/2013 | Rafferty |
| 2013/0211761 A1 | 8/2013 | Brandsma |
| 2013/0214300 A1 | 8/2013 | Lerman |
| 2013/0215467 A1 | 8/2013 | Fein |
| 2013/0225965 A1 | 8/2013 | Ghaffari |
| 2013/0237150 A1 | 9/2013 | Royston |
| 2013/0245388 A1 | 9/2013 | Rafferty |
| 2013/0274562 A1 | 10/2013 | Ghaffari |
| 2013/0313713 A1 | 11/2013 | Arora |
| 2013/0316442 A1 | 11/2013 | Meurville |
| 2013/0316487 A1 | 11/2013 | De Graff |
| 2013/0320503 A1 | 12/2013 | Nuzzo |
| 2013/0321373 A1 | 12/2013 | Yoshizumi |
| 2014/0001058 A1 | 1/2014 | Ghaffari |
| 2014/0012160 A1 | 1/2014 | Ghaffari |
| 2014/0012242 A1 | 1/2014 | Lee |
| 2014/0022746 A1 | 1/2014 | Hsu |
| 2014/0039290 A1 | 1/2014 | Favre |
| 2014/0097944 A1 | 4/2014 | Fastert |
| 2014/0110859 A1 | 4/2014 | Rafferty |
| 2014/0140020 A1 | 5/2014 | Rogers |
| 2014/0188426 A1 | 7/2014 | Fastert |
| 2014/0191236 A1 | 7/2014 | Nuzzo |
| 2014/0216524 A1 | 8/2014 | Rogers |
| 2014/0240932 A1 | 8/2014 | Hsu |
| 2014/0249520 A1 | 9/2014 | Ghaffari |
| 2014/0303452 A1 | 10/2014 | Ghaffari |
| 2014/0340857 A1 | 11/2014 | Hsu |
| 2014/0374872 A1 | 12/2014 | Rogers |
| 2014/0375465 A1 | 12/2014 | Fenuccio |
| 2015/0001462 A1 | 1/2015 | Rogers |
| 2015/0019135 A1 | 1/2015 | Kacyvenski |
| 2015/0035680 A1 | 2/2015 | Li |
| 2015/0069617 A1 | 3/2015 | Arora |
| 2015/0099976 A1 | 4/2015 | Ghaffari |
| 2015/0100135 A1 | 4/2015 | Ives |
| 2015/0194817 A1 | 7/2015 | Lee |
| 2015/0237711 A1 | 8/2015 | Rogers |
| 2015/0241288 A1 | 8/2015 | Keen |
| 2015/0260713 A1 | 9/2015 | Ghaffari |
| 2015/0272652 A1 | 10/2015 | Ghaffari |
| 2015/0286913 A1 | 10/2015 | Fastert |
| 2015/0320472 A1 | 11/2015 | Ghaffari |
| 2015/0335254 A1 | 11/2015 | Fastert |
| 2015/0342036 A1 | 11/2015 | Elolampi |
| 2016/0027834 A1 | 1/2016 | Graff |
| 2016/0045162 A1 | 2/2016 | De Graff |
| 2016/0081192 A1 | 3/2016 | Hsu |

FOREIGN PATENT DOCUMENTS

| | | |
|---|---|---|
| EP | 1808124 A2 | 7/2007 |
| EP | 2259062 A2 | 12/2010 |
| JP | 05-087511 A | 4/1993 |

(56) References Cited

FOREIGN PATENT DOCUMENTS

| | | |
|---|---|---|
| JP | 2009-170173 A | 7/2009 |
| WO | WO 99/38211 A2 | 7/1999 |
| WO | WO 03/021679 A2 | 3/2003 |
| WO | WO 2005/122285 A2 | 12/2005 |
| WO | WO 2007/003019 A2 | 1/2007 |
| WO | WO 2007/024983 A2 | 3/2007 |
| WO | WO 2007/116344 A1 | 10/2007 |
| WO | WO 2007/136726 A2 | 11/2007 |
| WO | WO 2008/030960 A2 | 3/2008 |
| WO | WO 2009/111641 A1 | 9/2009 |
| WO | WO 2009/114689 A1 | 9/2009 |
| WO | WO 2010/036807 A1 | 4/2010 |
| WO | WO 2010/042653 A1 | 4/2010 |
| WO | WO 2010/042957 A2 | 4/2010 |
| WO | WO 2010/046883 A1 | 4/2010 |
| WO | WO 2011/041727 A1 | 4/2010 |
| WO | WO 2010/056857 A1 | 5/2010 |
| WO | WO 2010/081137 A2 | 7/2010 |
| WO | WO 2010/082993 A2 | 7/2010 |
| WO | WO 2010/102310 A2 | 9/2010 |
| WO | WO 2010/132552 A1 | 11/2010 |
| WO | WO 2011/003181 A1 | 1/2011 |
| WO | WO 2011/084450 A1 | 7/2011 |
| WO | WO 2011/084709 A2 | 7/2011 |
| WO | WO 2011/127331 A2 | 10/2011 |
| WO | WO 2012/125494 A2 | 9/2012 |
| WO | WO 2012/166686 A2 | 12/2012 |
| WO | WO 2013/010171 A1 | 1/2013 |
| WO | WO 2013/022853 A1 | 2/2013 |
| WO | WO 2013/033724 A1 | 3/2013 |
| WO | WO 2013/034987 A3 | 3/2013 |
| WO | WO 2013/049716 A1 | 4/2013 |
| WO | WO 2013/052919 A2 | 4/2013 |
| WO | WO 2013/170032 A2 | 11/2013 |
| WO | WO 2014/007871 A1 | 1/2014 |
| WO | WO 2014/058473 A1 | 4/2014 |
| WO | WO 2014/059032 A1 | 4/2014 |
| WO | WO 2014/106041 A1 | 7/2014 |
| WO | WO 2014/110176 A1 | 7/2014 |
| WO | WO 2014/130928 A2 | 8/2014 |
| WO | WO 2014/130931 A1 | 8/2014 |
| WO | WO 2014/186467 A2 | 11/2014 |
| WO | WO 2014/197443 A1 | 12/2014 |
| WO | WO 2014/205434 A2 | 12/2014 |
| WO | WO 2015/021039 A1 | 2/2015 |
| WO | WO 2015/054312 A1 | 4/2015 |
| WO | WO 2015/077559 A1 | 5/2015 |
| WO | WO 2015/080991 A1 | 6/2015 |
| WO | WO 2015/102951 A2 | 7/2015 |
| WO | WO 2015/103483 A1 | 7/2015 |
| WO | WO 2015/103580 A2 | 7/2015 |
| WO | WO 2015/127458 A1 | 8/2015 |
| WO | WO 2015/134588 A1 | 9/2015 |
| WO | WO 2015/138712 A1 | 9/2015 |

OTHER PUBLICATIONS

Demura et al., "Immobilization of Glucose Oxidase with *Bombyx mori* Silk Fibroin by Only Stretching Treatment and its Application to Glucose Sensor," Biotechnology and Bioengineering, vol. 33, 598-603 (6 pages) (1989).

Ellerbee et al., "Quantifying Colorimetric Assays in Paper-Based Microfluidic Devices by Measuring the Transmission of Light through Paper," Analytical Chemistry, vol. 81, No. 20 8447-8452, (6 pages) (Oct. 15, 2009).

Halsted, "Ligature and Suture Material," Journal of the American Medical Association, vol. LX, No. 15, 1119-1126, (8 pages) (Apr. 12, 1913).

Kim et al., "Complementary Metal Oxide Silicon Integrated Circuits Incorporating Monolithically Integrated Stretchable Wavy Interconnects," Applied Physics Letters, vol. 93, 044102-044102.3 (3 pages) (Jul. 31, 2008).

Kim et al., "Dissolvable Films of Silk Fibroin for Ultrathin Conformal Bio-Integrated Electronics," Nature, 1-8 (8 pages) (Apr. 18, 2010).

Kim et al., "Materials and Noncoplanar Mesh Designs for Integrated Circuits with Linear Elastic Responses to Extreme Mechanical Deformations," PNAS, vol. 105, No. 48, 18675-18680 (6 pages) (Dec. 2, 2008).

Kim et al., "Stretchable and Foldable Silicon Integrated Circuits," Science, vol. 320, 507-511 (5 pages) (Apr. 25, 2008).

Kim et al., "Electrowetting on Paper for Electronic Paper Display," ACS Applied Materials & Interfaces, vol. 2, No. 11, (3318-3323) (6 pages) (Nov. 24, 2010).

Ko et al., "A Hemispherical Electronic Eye Camera Based on Compressible Silicon Optoelectronics," Nature, vol. 454, 748-753 (6 pages) (Aug. 7, 2008).

Lawrence et al., "Bioactive Silk Protein Biomaterial Systems for Optical Devices," Biomacromolecules, vol. 9, 1214-1220 (7 pages) (Nov. 4, 2008).

Meitl et al., "Transfer Printing by Kinetic Control of Adhesion to an Elastomeric Stamp," Nature, vol. 5, 33-38 (6 pages) (Jan. 2006)

Omenetto et al., "A New Route for Silk," Nature Photonics, vol. 2, 641-643 (3 pages) (Nov. 2008).

Omenetto et al., "New Opportunities for an Ancient Material," Science, vol. 329, 528-531 (5 pages) (Jul. 30, 2010).

Siegel et al., "Foldable Printed Circuit Boards on Paper Substrates," Advanced Functional Materials, vol. 20, No. 1, 28-35, (8 pages) (Jan. 8, 2010).

Tsukada et al., "Structural Changes of Silk Fibroin Membranes Induced by Immersion in Methanol Aqueous Solutions," Journal of Polymer Science, vol. 32, 961-968 (8 pages) (1994).

Wang et al., "Controlled Release From Multilayer Silk Biomaterial Coatings to Modulate Vascular Cell Responses" Biomaterials, 29, 894-903 (10 pages) (Nov. 28, 2008).

European Office Action for European Application No. 09 819 838.5, dated Oct. 5, 2015, (4 pages).

Japanese Office Action for Japanese Application No. 2014-225406, dated Nov. 4, 2015, with English translation, (9 pages).

\* cited by examiner

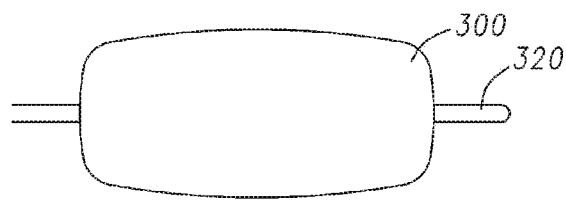
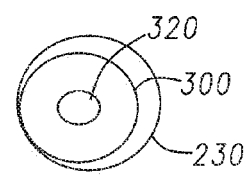
Fig. 3A
Fig. 3B
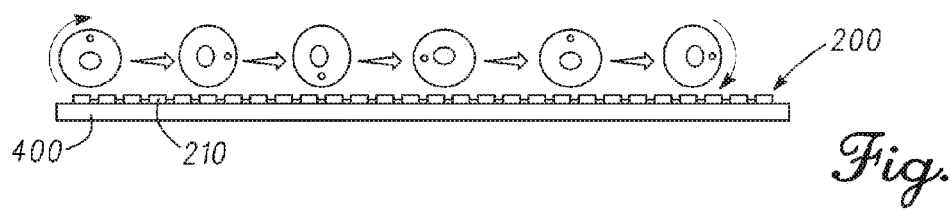
Fig. 3C
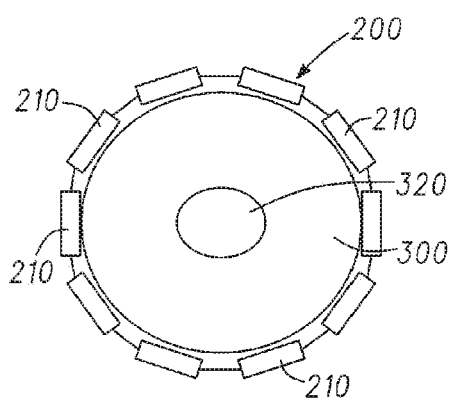
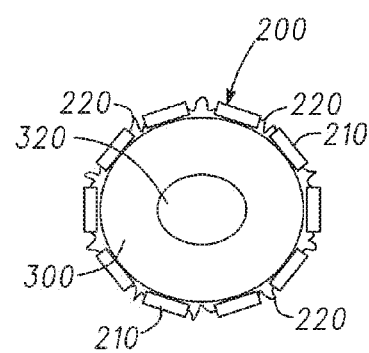
Fig. 3D
Fig. 3E

METHODS OF DETECTING PARAMETERS OF A LUMEN

CROSS-REFERENCE TO RELATED APPLICATIONS

This application is a division of U.S. Non-Provisional application Ser. No. 12/575,008, entitled "Catheter Balloon Having Stretchable Integrated Circuitry and Sensor Array," filed on Oct. 7, 2009, now allowed, which claims the benefit of U.S. Provisional Application No. 61/103,361, entitled "Catheter Balloon Sensor and Imaging Arrays" filed on Oct. 7, 2008, and U.S. Provisional Application No. 61/113,007, entitled "Catheter Balloon with Sensor and Imaging Array" filed on Nov. 10, 2008, each of which is hereby incorporated herein by reference in its entirety, including drawings.

FIELD OF THE INVENTION

The present invention relates to systems, apparatuses, and methods utilizing expandable or stretchable integrated circuitry and sensor arrays on expandable or stretchable materials, and in a particular, on balloon catheters.

BACKGROUND OF THE INVENTION

Intraluminal devices have become important in the diagnoses and treatment of a variety of medical conditions ranging from conditions associated with the digestive system to conditions related to the cardiocirculatory system. Current intraluminal sensing and therapeutic devices suffer from various disadvantages due to a lack of sophistication related to the sensing, imaging, and therapeutic functions. In some cases, such lack of sophistication resides in the fact that many such devices are configured with passive circuitry. Active integrated circuits utilizing multifunctional operative devices offer a variety sophisticated sensing, imaging, and therapeutic functions, including (but not limited to) pressure sensing, light imaging, and drug delivery. In the case where intraluminal devices have such active integrated circuits, such devices suffer from other disadvantages not the least of which is that such devices are unable to achieve direct contact with the part of the body being measured. The inability to achieve direct contact of such devices is attributable to the rigid nature of the operative devices and accompanying circuitry. This rigidity prevents devices from coming into full contact with soft, pliable, curved, and/or irregularly shaped tissue, which compromises accuracy of measurements.

By way of a non-limiting example, one such area where a need exists to obtain better contact and thus accuracy is in the area of analyzing arterial plaque deposits. Plaque deposits in the arterial lumen are widely recognized as a common cause of myocardial infarction, unstable angina, and even death. Plaques found inside the arterial lumen are classified as 'vulnerable' or 'stable.' These two types of plaque have significantly different compositions that give rise to variations in electrical, thermal, chemical, and material properties. Vulnerable plaque consists of a lipid core containing large amounts of cholesterol deposits, inflamed cells (macrophages), low levels of collagen and other matrix proteins. The collagen and associated fibrous proteins are found as a thin surface layer, encapsulating all of the other structural components. Based on size and the effects of shear stress exerted by the flow of blood, the enclosure formed by the thin fibrous caps is susceptible to mechanical rupture. The rupture and subsequent release of the deposits internal to the plaque is a key mechanism underlying thrombosis and myocardial infarctions.

In contrast, stable plaque is much less susceptible to rupture and thus is far less dangerous. Stable plaques have a significantly more robust outer shell, consisting of a thick fibrous cap. Although stable plaques can cause significant stenosis that may require intervention, the effect of arterial occlusion is much less harmful than the rupture of vulnerable plaque. It is important to note that the vulnerable plaque typically form a narrowing of less than 50%, suggesting that the deleterious effects of a vulnerable plaque cannot be predicted based on the extent of occlusion alone. Moreover, it is difficult to distinguish between vulnerable and stable plaque based purely on extracorporeal imaging techniques.

One direct way to detect the presence of vulnerable plaque is through temperature and pressure sensing near the plaque site, since plaque has non-uniform surface contours and because there is a significant difference in the temperature of vulnerable plaque compared to that of the normal lumen and stable angina. But current temperature sensors are fabricated on rigid supports and embedded within the catheter body. One such sensor is located at the center of the lumen in the catheter. This design requires compensation for the distance separating the temperature sensor from the plaque wall. Adjustments in temperature recordings are made based on a displacement sensor that senses the distance between the plaque wall and the catheter within the lumen. Although this type of device can theoretically estimate the temperature at the plaque, complications and errors can arise.

SUMMARY OF THE INVENTION

In embodiments, the present invention may be a device that includes an inflatable body having a surface, and a stretchable electronic circuit comprising at least one discrete operative device being in electronic communication with at least one other discrete operative device, where the stretchable electronic circuit may be affixed to the inflatable body.

The stretchable electronic circuit may comprise a single crystalline semiconductor structure, and may be a printable electronic circuit. The stretchable electronic circuit is operable when the inflatable body is inflated even when the inflatable body is inflated, up to 150 and in some cases, up to 300 percent of its original size.

The electronic communication between the operative devices may be wireless. The operative devices may further comprise a transceiver receiving data from the discrete operative device. Alternatively, electronic communication may be through a physical electrical connection. This physical electrical connection may be stretchable. In some embodiments the physical electrical connection is configured to buckle when the inflatable body is deflated. In some embodiments the physical electrical connection is configured to be non-coplanar with the inflatable body when the inflatable body is relaxed, and be coplanar with the inflatable body when the inflatable body is inflated. The inflatable body may be made of a polymer. The inflatable body may be a balloon, which in some embodiments, may be fitted with a stent.

In embodiments, the discrete operative device may include an amplifier, a semiconductor structure, a transducer, a sensor, and the like. Such sensors may detect temperature, capacitance, pressure, reflectivity, chemicals, enzymatic activity, and mechanical properties. In some embodiments the device is in communication with a processor programmed to generate data for an image related to a body lumen, such as spatial, temperature, tactile image, visual map, and the like.

The operative device may include a sensor, where the operative device may continuously generate data, and where the continuously generated data may be recorded.

Further, the device of the present invention may comprise a drug delivery polymer comprising a drug, where the stretchable electronic circuit may activate the drug delivery polymer.

In embodiments, the present invention provides a method, the method being executed by a processor programmed to perform the steps of the method. In embodiments the method is to detect parameters inside a lumen, including inserting a device of the present invention into a lumen, inflating the inflatable body, contacting the lumen, measuring a parameter of the lumen. Further, the present invention may deliver a therapy based on the measurement, and generate a graphical output based on said measured parameter.

BRIEF DESCRIPTION OF THE DRAWINGS

FIGS. 3A-E show fabrication steps related to embodiments of the present invention.

DETAILED DESCRIPTION OF THE INVENTION

As described herein, the present invention comprises devices, systems, and methods utilizing stretchable electronic circuits on expandable or inflatable surfaces. With reference to the present invention, the term "stretchable", and roots and derivations thereof, when used to modify circuitry or components thereof is meant to encompass circuitry that comprises components having soft or elastic properties capable of being made longer or wider without tearing or breaking, and it is also meant to encompass circuitry having components (whether or not the components themselves are individually stretchable as stated above) that are configured in such a way so as to accommodate and remain functional when applied to a stretchable, inflatable, or otherwise expandable surface. The term "expandable", and roots and derivations thereof, when used to modify circuitry or components thereof is also meant to have the meaning ascribed above. Thus, "stretch" and "expand", and all derivations thereof, may be used interchangeably when referring to the present invention.

Figure 1:
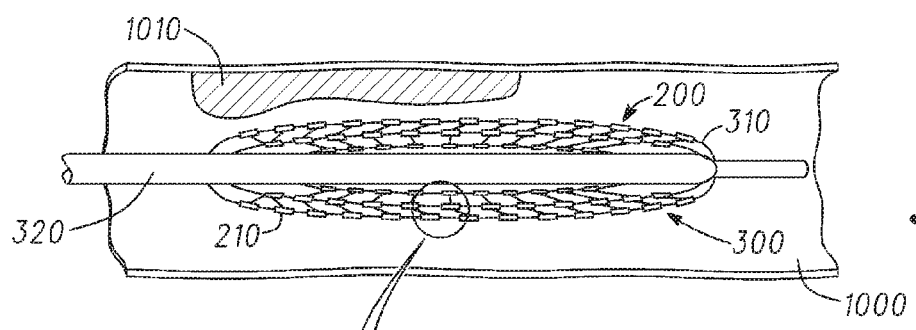
FIG. 1 shows an embodiment of the invention in a deflated state and inside a body lumen.

FIG. 1 shows an embodiment of the invention wherein a stretchable electronic circuit 200 is on an expandable body 300. In embodiments such as the one shown in FIG. 1, the expandable body 300 is inflatable and in some embodiments (such as the one shown in FIG. 1) the inflatable body is a balloon on a catheter. The skilled artisan will appreciate that the balloon and catheter together are referred to as a "balloon catheter", which is a type of catheter with an inflatable balloon at its tip and which is used during a catheterization procedure for various medical procedures such as to enlarge a narrow opening or passage within the body. The deflated balloon catheter is positioned, then inflated to perform the necessary procedure, and deflated again in order to be removed.

FIG. 1 shows the balloon catheter in a relaxed or deflated state, which is inserted into a lumen 1000 which, in this embodiment is an artery. FIG. 1 shows arterial plaque 1010 formed on the inner wall of the artery. The stretchable electronic circuitry 200 is on the surface of the inflatable body 300 and will be discussed in more detail below.

In embodiments, the circuitry 200 utilizes complementary metal-oxide semiconductor (CMOS) technology. CMOS devices offer a variety sophisticated sensing, imaging, and therapeutic functions, including (but not limited to) pressure sensing, light imaging, and drug delivery. The device arrays are designed to withstand stretching and bending and can be embedded in or affixed onto a stretchable surface, such as that made of a polymer material.

Figure 1A:
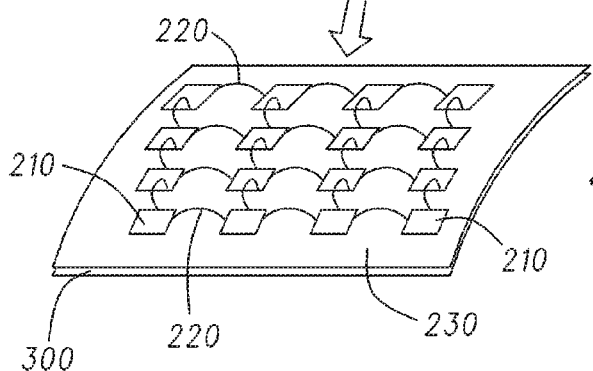
FIG. 1A is an expanded view of a portion of FIG. 1.
Figure 2:
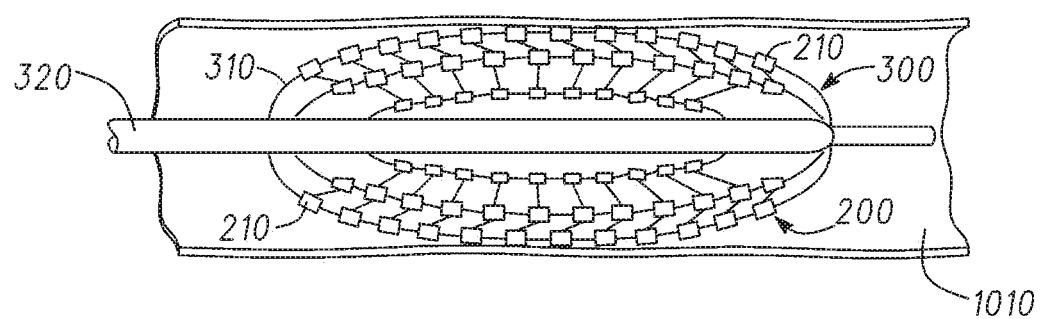
FIG. 2 shows an embodiment of the invention in an inflated state and inside a body lumen.

FIG. 1A shows a detailed view the circuitry 200 of the claimed invention while the device is in a deflated or unexpanded state. The circuitry 200 of the invention comprises at least one operative device 210 which is, in embodiments, in electronic communication with at least one other operative device 210. In embodiments, the operative devices are discrete (in embodiments, arranged in a "device island" arrangement as described below) and are themselves capable of performing the functionality described herein, or portions thereof. In embodiments, such functionality of the operative devices 210 can include integrated circuits, physical sensors (e.g. temperature, pH, light, radiation etc), biological and/or chemical sensors, amplifiers, A/D and D/A converters, optical collectors, electro-mechanical transducers, piezo-electric actuators, light emitting electronics which include LEDs, and combinations thereof The purpose and advantage of using standard ICs (in embodiments, CMOS, on single crystal silicon) is to have and use high quality, high performance, and high functioning circuit components that are also already commonly mass-produced with well known processes, and which provide a range of functionality and generation of data far superior to that produced by a passive means. For purposes of the invention, passive systems are defined by their absence of local amplification, and/or a lack of the ability to perform (on-board) any the functionality described above and herein. In order to accommodate the discrete operative devices 210, which may be rigid, to the demands of an expandable and stretchable substrate 300 such as a catheter balloon, the operative devices 200 are fabricated such that they are located in discrete and isolated "device islands" and are electrically interconnected by stretchable interconnects, or interconnects configured to accommodate an expandable or stretchable surface. The interconnects are referred to as 220. In the embodiment shown in FIG. 1A, it can be seen that the interconnects 220 are flexible and thus able to accommodate the stretching caused by the inflation of the balloon 300 (shown in FIG. 2). Thus, the entirety of the circuitry 200 is expandable or stretchable. In the embodiment shown in FIG. 1A, the interconnects 220 are buckled or non-coplanar when the balloon 300 is in a deflated state. When the balloon 300 is inflated (as shown in FIG. 2), the interconnects 220 become either coplanar or non-buckled so as to accommodate the increased distance between the discrete operative devices 210 upon inflation. Additionally, serpentine interconnects may be used.

In embodiments, the electronic communication between the discrete operative devices and/or between said devices and separate devices could be wireless. Therefore, said devices may comprise a transducer, transmitter, or receiver capable of such wireless transmission.

The specific fabrication method for such circuitry may depend on the specific circuit classes desired to incorporate into the device, and the specific characteristics of the circuitry, including those of the discrete operative devices, the interconnects, etc., include, but are not limited to, those disclosed in the following references each of which is incorporated herein by reference in its entirety: U.S. Pat. No. 7,557,367 to Rogers et al. entitled "Stretchable Semiconductor Elements and Stretchable Electrical Circuits"; Ko et al., "A hemispherical electronic eye camera based on compressible silicon optoelectronics," Nature (2008) (which is attached the '007 provisional Appendix B and is referred to in the '361 provisional); D.-H. Kim, W. M. Choi, J.-H. Ahn, H.-S. Kim, J. Song, Y. Huang, Z. Liu, C. Lu, C. G. Koh and J. A. Rogers, "Complementary Metal Oxide Silicon Integrated Circuits Incorporating Monolithically Integrated Stretchable Wavy Interconnects," Applied Physics Letters 93, 044102 (2008) (which is attached to the '007 provisional as Appendix C); D.-H. Kim, J.-H. Ahn, W.-M. Choi, H.-S. Kim, T.-H. Kim, J. Song, Y. Y. Huang, L. Zhuangjian, L. Chun and J. A. Rogers, "Stretchable and Foldable Silicon Integrated Circuits," Science 320, 507-511 (2008) (which is attached to the '007 provisional as Appendix D); R. Dinyari et al, K. Huang, S. B. Rim, P. B. Catrysse and P. Peumans, "Curved silicon focal plane arrays," Appl. Phys. Lett. (2008) (which is attached to the '007 provisional as Appendix E and is referred to in the '361 provisional). Also to provide fabrication methods for such stretchable circuitry and to describe the specific characteristics of the circuitry, including those of the discrete operative devices, the interconnects, etc., are discussed in the following references, each of which is incorporated herein by reference in its entirety: United States Published Patent Application No. 2006/0286488 entitled "Methods and Devices for Fabricating Three-Dimensional Nanoscale Structures"; U.S. Pat. No. 7,195,733 to Rogers et al. entitled "Composite Patterning Devices for Soft Lithography"; U.S. Pat. No. 7,521,292 to Rogers et al. entitled "Stretchable Form of Single Crystal Silicon for High Performance Electronics on Rubber Substrates"; United States Published Patent Application No. US 2009/0199960 for Rogers et al. entitled "Pattern Transfer Printing by Kinetic Control of Adhesion to an Elastomeric Stamp"; United States Published Patent Application. No. 2007/0032089 for Nuzzo et al. entitled "Printable Semiconductor Structures and Related Methods of Making and Assembling"; United States Published Patent Application No. 2008/0157235 for Rogers et al. entitled "Controlled Buckling Structures in Semiconductor Interconnects and Nanomembranes for Stretchable Electronics"; United States Published Patent Application No. 2008/0108171, Release Strategies for Making Transferable Semiconductor Structures, Devices and Device Components, and also U.S. patent applications having the following Ser. No. 11/145,574 entitled "Methods and Devices for Fabricating and Assembling Printable Semiconductor Elements, filed Jun. 2, 2005, Ser. No. 11/675,659 entitled "Devices and Methods for Pattern Generation by Ink Lithography, filed Feb. 16, 2007, and Ser. No. 12/398,811 entitled "Stretchable and Foldable Electronic Devices", filed on Mar. 5, 2009.

Such circuits may be applied to the surface of the balloon or to a stretchable or expandable material that may be wrapped around the balloon via transfer printing of partially or wholly processed single-crystal silicon devices, using methods described in the aforementioned references or also methods in M. A. Meitl, Z.-T. Zhu, V. Kumar, K. J. Lee, X. Feng, Y. Y. Huang, I. Adesida, R. G. Nuzzo and J. A. Rogers, "Transfer Printing by Kinetic Control of Adhesion to an Elastomeric Stamp," Nature Materials 5, 33-38 (2006) (attached to the '007 provisional as Appendix F).

A non-limiting example of the complete fabrication steps of an embodiment of the invention, i.e., a catheter balloon instrumented with temperature sensors, is described in the following paragraphs. It should be noted that while the embodiment described below refers to an inflatable system (specifically a catheter balloon), the skilled artisan will appreciate that such principals of operation will apply to situations where the body on which the circuitry is applied is otherwise stretchable or expandable but not inflatable.

Arrays of discrete operative devices 210, which may include temperature sensors and associated differential amplifiers, buffers, A/D converters, logic, memory, clock and active matrix switching transistors are laid out in a "device island" arrangement. The device islands can be 50 tm×50 tm squares, most of which accommodate a single conventional sensor circuit, e.g., a temperature sensor, connected to a buffer, that itself connected to an amplifier. The temperature sensor, which may be resistive, diode-based, etc., as described in greater detail below, supplies a signal that reflects temperature (or a temperature change), and the remaining sensor circuitry conditions the signal for subsequent processing.

In embodiments, discrete operative devices 210 accommodate active matrix switches and A/D converters for transforming an analog temperature signal into digital form, and some operative devices accommodate logic circuitry capable of reading in digital signals and processing them (e.g., to assign a value to the sensed temperature or temperature change). These circuits may output the temperature reading to another module or, and are capable of outputting data or storing it in on-board memory cells.

The circuitry is arranged and designed such that preferably only about one, but not more than about 100 electrical interconnections are required between any two device islands. In embodiments, the circuits are then fabricated on an SOI wafer (although it should be understood that standard wafers could be used) (1.2 µm thick top Si, 1 µm thick buried oxide) using standard CMOS fabrication technology, and the silicon space in between each island is etched away to isolate each island. The circuits are protected by a polyimide passivation layer, then a short HF etch is done to partially undercut the islands. The passivation layer is removed, and then a thin film of SiO2 is deposited and patterned (100 nm thick) by PECVD or other deposition technique combined with a liftoff procedure, such that the oxide layer covers most of the space between discrete operative devices except for a region around each device island that is about 5 µm wide. This will be an additional sacrificial material for subsequent use in the fabrication process. Another polyimide layer is spun on and patterned into the shape of the interconnects. Typically one interconnect may extend from the center of one device to the center of another device. Alternately, two interconnects may extend from each corner of the device to two different device corners. Other interconnect configurations are understood. The interconnect bridges may be about 25 µm wide and may accommodate multiple electrical lines. The polyimide partially fills underneath the device island where it is undercut; this serves to stabilize the island later in the release process and prevent it from floating away. VIAS are etched into the PI layer to allow metal wires, patterned in the next step, to contact the circuits and connect one island to another. (This step can be repeated to form additional sets of wires located above the first set.) Another PI layer is spun on (covering the wires and everything else). The PI (both layers) is then isolated by etching with a deposited SiO2 hard mask, in O2 RIE. PI located outside the devices and bridges is etched, as well as PI covering areas that are meant to be externally electrically interfaced, and small areas leading to the underlying oxide. Etch holes may be formed if necessary and then transferred through the silicon or metal layers by wet and or dry etching. The underlying buried oxide is etched away using HF etchant to free the devices, which remain attached to the handle substrate due to the first polyimide passivation layer which contacts the handle wafer near the border around the devices.

If the HF etch is not controllable enough and finds a way to seep under the PI isolation layer and attack the CMOS devices, then prior to the first PI passivation a short Argon sputtering can be done to remove any native oxide followed by amorphous silicon sputtering followed by the PI passivation and the rest of the processing.

After rinsing, the devices are left to air dry. After drying, they are picked up with a PDMS stamp, and transfer printed onto either the surface of an expandable/inflatable body 310, or a surface of an expandable/inflatable body coated with a thin PDMS layer, or a separate thin PDMS layer (that may later be wrapped around the balloon). FIG. 3A shows a side view of a balloon with the PDMS layer 230 wrapped around the surface of the balloon 300. FIG. 3B is a cross-sectional view which shows the catheter 320, the surface of the balloon 300, and the thin PDMS layer 230 applied to the balloon 300.

It is also possible for a thin PDMS mold to be made of half the (inflated) balloon shape, such that it can be stretched flat, and have circuits transferred onto it in the flat state, and then released to pop back into the half-balloon shape; this half-balloon can then be easily attached to the real balloon, and may even be glued. It is noted that in all transfer cases, the circuits are on the outside of the balloon, and the bridges (also referred to as interconnects and physical electrical connections herein) pop or buckle outward when the devices are compressed or the expandable/inflatable body is otherwise in a relaxed or deflated state. In the inflated state, the bridges should be fairly non-buckled and/or coplanar with the surface of the inflatable body 300 so that in the deflated state they can buckle to accommodate the significant compressive stress. Alternately this process can be repeated with a mold made in the deflated state of the balloon, and stretched beyond flat so that it is significantly expanded, such that after the circuits are transferred and the mold is released, they compress significantly. In this case, they should be compressed enough so that after transfer to the real balloon, when it is fully expanded, the bridges are nearly flat or fully extended and almost non-buckled.

In the case where the circuitry 200 is directly transferred to the balloon, the PDMS stamp should be made thin (~100-500 µm in thickness) and thereby compliant enough to conform to the shape of the balloon.

In the case where the circuitry is first transferred to a separate thin PDMS layer, the PDMS layer may be on a rigid substrate so that the transferring can be done easily. Then the PDMS layer can be peeled off the substrate and wrapped around the balloon either in the inflated or deflated state, depending on whether the circuitry was transferred with any prestrain or not. It may be desirable to make the circuitry in a 1D array rather than a 2D array. In this way, the thin PDMS layer is a long, narrow ribbon that can be easily wrapped around the balloon so as to cover the entire balloon surface. Alternatively, if it is desired that the circuitry face inwards to the balloon, the balloon can be directly rolled along a planar array of circuitry 200 on PDMS carrier substrate 400 as shown in FIG. 3D. The balloon can be subsequently deflated and/or re-inflated. Deflation can cause the interconnects in the circuitry to buckle and take on compression forces imposed by deflation as shown in FIG. 3E. It should be understood that these stamping methodologies applied to the balloon catheter can be applied to stamp the electronic circuitry in all of the embodiments described below.

In embodiments where the circuitry is facing outwards on the balloon, it may be encapsulated (while in its compressed state) with another layer of PDMS, or a liquid layer of PDMS followed by an upper layer of solid PDMS to make a fluid encapsulation.

In embodiments where the circuitry is facing outwards on the balloon, the circuitry may be electrically externally interfaced at conductive pads that should be designed to be located at the base of the balloon. Anisotropic conductive film (ACF) connectors can be used to interface to these conductive pads, by pressing and heating the film onto the pads. The film can then run down the length of the catheter since it is so thin and flexible.

In embodiments where the circuitry is encapsulated or facing inwards, the circuitry may be electrically externally interfaced by first removing part of the encapsulating polymer over the conductive pads through wet or dry chemical etching, or physical mechanical removal of material, including but not limited to drilling. At this point, the ACF may be incorporated. Alternatively, the stretchable circuitry may be electrically interfaced to an ACF prior to the transfer or encapsulation process.

In embodiments, it may be possible for the circuitry to be powered externally optically, using the catheter tube as a waveguide and having PV cells made in a stretchable format in addition to the rest of the circuitry. In addition, LED islands may be made to perform optical data communication down the catheter waveguide. Alternately, thin film batteries may be used to power the circuitry. Alternately, RF communication circuits on the device may be used to wirelessly communicate outside of the body, and may also receive RF power to power the circuits. Using these approaches, the need for external electrical interfaces may be eliminated.

In one embodiment, the stretchable substrate is typically polymeric, e.g., polyimide or polydimethylsiloxane (PDMS). The single-crystal semiconductor devices themselves may be created on a silicon-on-insulator (SOI) carrier wafer in accordance with a circuit design implementing the desired functionality. Interconnect systems may also be created during this step to join smaller circuit islands. The processed single-crystal devices are removed from the SOI wafer (e.g., by etching) and are then placed in contact with an elastomeric stamp for transfer printing (via soft lithography) onto the desired flexible polymer substrate.

The circuitry is then transferred onto the stretchable substrate, which may be pre-stretched prior to transfer. The stretchable substrate serves as the catheter balloon, and can be conformed to the shape of an inflated balloon by a mold. The balloon polymer can be stretched over large strains (greater than 300 percent) without causing damage to the circuitry. The circuitry can be encapsulated with additional thin polymer layers to provide further protection from cracks or local contact stresses.

It is understood that stretchable circuitry may be realized using techniques other than those described above, combinations of the techniques listed above, and minor deviations from the techniques described above as will be apparent to those skilled in the art the art. For example, stretchable circuits may be formed on plastic, elastomeric, or other stretchable materials by sputtering, chemical vapor deposition, ink jet printing, or organic material deposition combined with patterning techniques. Semiconductor materials which may be used to make circuits may include amorphous silicon, polycrystalline silicon, single crystal silicon, conductive oxides, carbon annotates and organic materials. Islands of silicon connected by spiral interconnects made by surface micromachining or bulk etching may also be employed.

In use, an inflatable body 300 covered with stretchable circuitry 200 having an array of discrete operative devices 210 may be inserted in a lumen 1000. The discrete operative devices may include temperature sensors. The temperature sensors may be, for example, silicon band gap temperature sensor, consisting of silicon diodes. The forward voltage of these silicon diodes are sensitive to changes in temperature. Alternatively, platinum thin-film resistance temperature devices (RTD), which measure temperature based on temperature-induced changes in electrical resistance or thermocouple circuits that sense temperature changes between different thermoelectric materials can be utilized. For thermal resistors, the normalized changes in resistance (R), temperature coefficients of resistors (a), are related to the change in temperature (T) by $$\Delta R/R = \alpha T.$$

Platinum (500 Å) and an adhesion layer of chromium (150 Å) can be patterned and deposited on SOI wafers using thermal evaporation via e-beam to define individual RTD sensors. The RTD sensors can be integrated with CMOS based amplifiers, transducers, computation logic elements, and A/D circuitry on the same device islands as previously described.

Once the circuitry 200 is transferred onto the expandable body, in this embodiment, a balloon catheter 300, stretching and fatigue tests can be performed with a mechanical bending stage, capable of applying uneasily tensile or compressive strains in multiple directions or by repetitive inflation and deflation loading cycles. The mechanical bending stages can work in parallel with electrical probing stations (Agilent, 5155C) that are coupled to the circuit semiconductors. In embodiments, to evaluate the performance of the circuitry, multiple cycling of heating and cooling tests can be performed. The circuits can be heated to 160° C. for 5 min. and subsequently cooled down before and after each electrical measurement.

To protect the circuitry from external damage, an encapsulating thin layer of polymer can be applied to the circuitry, including on the surface of the inflatable body after the circuitry is applied thereto. This encapsulating polymer layer may be extremely thin (<100 µm) and photocurable, in order to allow selective curing in regions where direct contact with sensors is not required. In the embodiment described above, the RTD temperature sensors may be preferentially exposed for direct contact during photocuring. There are several polymers that may be used for preferential photocuring of the encapsulating layer, including but not limited to polyethylene glycol (PEG) with 2-hydroxy-2-methylpropiophenone photoinitiator. The photocurable PEG encapsulation cures once it is exposed to ultraviolet light. Photomasks designed using AUTOCAD can be printed to allow preferential curing of the surface of the inflatable body. These masks can be inserted as a filter into a UV light source stage coupled with a wide excitation UV filter. Exposure with an aligned mask enables polymerization in strategic regions of the inflatable body. Visual alignment during polymerization can be achieved with a CCD camera.

In embodiments, the inflatable body instrumented with an array of operative devices including temperature sensors can be deployed such that the temperature sensors are positioned in direct contact with the surface of plaque in the lumen upon inflation of the inflatable body. In such embodiments, the separation distance between sensors can be any that is manufacturable, a useful range may be, but is not limited to, 10 µm-10000 µm. Individual sensors may be coupled to a differential amplifier, and/or a buffer and/or an analog to digital converter. These circuits may be formed on the same, or different, discrete operative devices than the temperature sensors. The circuits may be laid out in an active matrix fashion such that the readings from multiple temperature sensors can be switched into and processed by one or a few amplifier/logic circuits. These sensor arrays record input signals that can then be channeled from the surface of the balloon to guidewires and a processor using metal electrodes deposited near the junction between the balloon surface and the catheter tubing. Alternatively, gold metal wires may be used to attach the balloon circuitry to the surface of the catheter guidewire using a wire bonder. Signals from the array of sensors can be processed using multiplexing techniques, including those described in published international patent application WO2009/114689 filed Mar. 12, 2009 the entirety of which is hereby incorporated herein by reference. Multiplexor component circuitry located in the base of the catheter guidewire can facilitate this type of data analysis/processing.

The device operator may use optical guidance during an x-ray angiography to deploy the balloon catheter once the guidewire reaches the region of the plaque location. The deformable and stretchable nature of the catheter balloon allows temperature measurements at multiple contact points on non-uniform surface contours such as that of arterial lumen and deposited plaque (shown as 1010 in FIGS. 1 and 2B). Once deployed, the interface electronics process the transmitted signals and produce a spatial temperature map of the plaque in the lumen. This data can be used by the device operator to detect temperature heterogeneity presence along the plaque and determine plaque type. Once plaque type is determined and surface contours are characterized, the balloon catheter can be deflated and removed.

Figure 4:
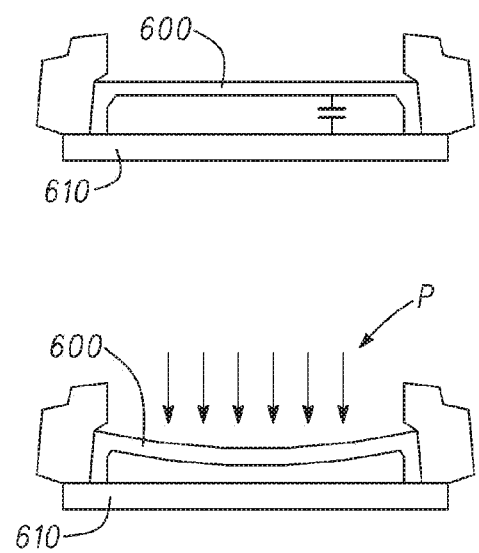
FIG. 4 is an embodiment of a sensor of the present invention.

In another embodiment of the invention, the stretchable circuitry comprises pressure sensor arrays. Such sensor arrays may be silicon-based and utilize piezo-resistive or capacitive sensing, or may be polymer based or optically based. In embodiments, a pressure sensor should have a working range and size suitable to the application, and should be amenable to application as described herein and tolerant to the stretching forces it will experience. FIG. 4 shows one exemplary pressure sensor which comprises a flexible and suspended diaphragm 600 of a flexible material such as thin single-crystal silicon, polysilicon, and/or silicon nitride thin film. The diaphragm 600 can be suspended directly above a base layer of doped silicon consisting of a metal electrode layer extracted from an SOI wafer. The polysilicon diaphragm layer may be formed as a suspended layer by first depositing an SiO2 layer on the silicon electrode 610. The polysilicon may then be deposited on the SiO2 layer, which in turn can be selectively etched. This etching step allows for the formation of a suspended and flexible polysilicon structure. In order to produce diaphragms with a controlled thickness, precise etch rates using HF must be used. This diaphragm with known thickness (2-10 µm thick), material modulus, and surface area and the underlying silicon electrode collectively form a parallel-plate capacitor. The sensor capacitance is a function of distance between the top polysilicon layer and the underlying silicon electrode. The capacitance recordings relate diaphragm deflection (caused by force P) to changes in capacitance.

In embodiments of the invention, the stretchable circuitry comprises an array of contact sensors. The contact sensors are designed to provide an on/off electrical resistance change in response to a pressure, such that when the applied pressure exceeds a predetermined threshold, the sensor provides an electrical signal indicating that it is in contact with, e.g., the arterial wall. One example of how to form a contact sensor is to make a simple mechanical-electrical switch, in which one conductor is mechanically pressed onto another conductor. The lower conductor, located on the surface balloon, consists of a metal wire that is non-continuous in one or more places to form an open circuit. Encapsulated around this open circuit is a diaphragm formed out of PDMS. The PDMS may be molded or etched into a diaphragm shape. The upper wall of the diaphragm is coated with a metal conductor, by standard means of photolithography patterning, electrochemical etching, etching, shadow evaporation, etc. The diaphragm is aligned and bonded to the surface of the balloon. The diaphragm is designed so that when a certain pressure is applied, it bends down to allow the upper conductor to contact and short-circuit the lower non-continuous conductor. This is done by control of the geometry (height and width) and materials of the diaphragm. In yet another non-limiting example, the diaphragm may be made with MEMS techniques, such as sacrificial silicon dioxide layers with a polysilicon bridge on top.

In embodiments of the invention, to measure relative pressure, each pressure sensor can be coupled with reference sensor unit, which has identical electrical characteristics except for a significantly lower pressure sensitivity. Difference in pressure measurements between the sensor and the reference unit enable compensation for many parasitic effects. The reference units may be created by leaving a passivation layer on the top surface of the polysilicon electrode. Having a reference unit along with a pressure sensor unit allows for differential pressure recordings. Once deployed, such sensor arrays can sense the presence and mechanical properties of the arterial lumen and plaque. They may also be used to estimate the diameter of the balloon and the lumen and provide feedback to the device operator to end balloon inflation at this point. This type of sensing can be combined with temperature sensor arrays to provide a thorough assessment of tissue mechanical and thermal properties during a single balloon deployment attempt. Pressure sensing also allows for creation of a tactile image map of the surface contours of the plaque. This type of mechanical imaging in a balloon catheter can indicate whether a stent has been successfully deployed when the balloon is inflated.

In embodiments of the invention, the plaque type is initially determined with temperature sensors and immediately afterwards, drug-delivery polymers and circuitry embedded in the balloon polymer are activated to cause local cooling and/or release of chemical agents, such as anti-inflammatory drugs, to local sites on the plaque where inflammation is present. In embodiments, light emitting electronics (such as LED) could be utilized to activate a drug delivery polymer.

In embodiments of the invention, the stretchable circuitry comprises packed array of active pixel sensors. Each pixel in the array may contain a photodetector, a pn junction blocking diode, an active amplifier, and an analog to digital converter, formed in a single piece of single crystalline silicon (50×50 µm2; 1.2 µm thick). These fabricated operative devices are fabricated in accordance with, for example, in Ko et al., "A hemispherical electronic eye camera based on compressible silicon optoelectronics," Nature (2008). In this embodiment, all of the circuitry may be encapsulated with a polymer layer such as PDMS to prevent contact stress induced damage of circuitry on the inflatable body, since there is no requirement for direct contact of the lumen with photosensor arrays. An array of photodetectors on the inflatable body positioned in close proximity to the plaque site within a the arterial lumen can provide high spatial resolution imaging without the need for a lens-based focusing due to the proximity of the photodetectors to the lumen. The catheter guidewire may comprise a light source, such as an optical fiber or an LED to provide illumination to the photodetectors for imaging the plaque and lumen surface.

In embodiments of the invention, the inflatable body is covered with ultrasound emitters and receivers to produce a lateral deep-tissue image of the plaque and arterial lumen.

In embodiments of the invention, the inflatable body is covered with stimulating and recording electrodes used for measuring plaque conductivity. Since vulnerable plaque is significantly less conductive than stable plaque and arterial tissue, this form of sensor array can help determine the plaque type based on measured conductivity of the plaque. Once the inflatable body is deployed, the electrodes are positioned in direct contact with the plaque deposits and electrical conductivity is measured. Again, this device can be combined with other sensor array types embedded in the stretchable inflatable body to provide multiple sensing and therapeutic functionalities in parallel.

Data collected by sensors at the site of the plaque can be interpreted against a baseline established by deploying the same inflatable body (or a second inflatable body on the same catheter) at a different location, which is free of plaque, in the lumen.

In embodiments of the invention, the array of operative devices includes temperature detectors, pressure sensors, and photodetectors collectively fabricated in a flexible and stretchable polymer-based balloon catheter substrate. These active device components can be designed using 0.6 µm design feature resolution or smaller. They may be integrated on the operative devices that are pieces of single crystalline silicon (50×50 µm2; 1.2 µm thick). Once the balloon is inserted in the arterial lumen, the device operator navigates the guidewire leading the balloon to the plaque location. The deployment of the balloon can stop blood flow intermittently. The guidewire is preferably fitted with an optical fiber or LED; the close contact of the imaging arrays to the lumen avoids the need for optical lens arrays, since light from the optical source may pass through the interconnect gap regions between the arrays, scatter through the lumen/plaque, and reach the photodetectors directly.

In this embodiment, the pressure sensor array detects when the inflatable body initially contacts the plaque and spatially maps the entire region of contact to ensure successful deployment. Temperature sensors continuously record data and spatially map temperature as a way to detect where in the arterial plaque there may be inflammation and macrophage deposits. The device operator may examine the data and decide whether to take immediate action through drug-delivery measures, stent deployment, or further tests on the plaque. The device operator may also utilize light imaging to visualize the plaque. Having integrated pressure sensors and imaging sensor arrays on the balloon, in addition to temperature sensors, allows for creation of a detailed tactile and visual map of the regions where the balloon contacts the plaque. This type of distributed mechanical sensing and imaging with an array of pressure sensors and photodetectors ensures that the stent and/or balloon contact the entire surface of the plaque. This embodiment of the balloon catheter can be deployed with a stent that may be fitted around the active sensing and imaging regions of the balloon.

The methods and systems described in connection with the invention described herein (the "Subject Methods and Systems") may be deployed in part or in whole through a machine that executes computer software, program codes, and/or instructions on a processor. The active stretchable circuitry described herein may be considered the machine necessary to deploy the Subject Methods and System in full or in part, or a separately located machine may deploy the Subject Methods and Systems in whole or in part. Thus, "machine" as referred to herein may be applied to the active circuitry described above, a separate processor, separate interface electronics or combinations thereof.

The Subject Methods and Systems invention may be implemented as a method on the machine, as a system or apparatus as part of or in relation to the machine, or as a computer program product embodied in a computer readable medium executing on one or more of the machines. The processor may be part of a server, client, network infrastructure, mobile computing platform, stationary computing platform, or other computing platform. A processor may be any kind of computational or processing device capable of executing program instructions, codes, binary instructions and the like. The processor may be or include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable execution of multiple programs, threads, and codes. The threads may be executed simultaneously to enhance the performance of the processor and to facilitate simultaneous operations of the application. By way of implementation, methods, program codes, program instructions and the like described herein may be implemented in one or more thread. The thread may spawn other threads that may have assigned priorities associated with them; the processor may execute these threads based on priority or any other order based on instructions provided in the program code. The processor, or any machine utilizing one, may include memory that stores methods, codes, instructions and programs as described herein and elsewhere. The processor may access a storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual core processor, quad core processors, other chip-level multiprocessor and the like that combine two or more independent cores (called a die).

The Subject Methods and Systems described herein may be deployed in part or in whole through a machine that executes computer software on a server, client, firewall, gateway, hub, router, or other such computer and/or networking hardware. The software program may be associated with a server that may include a file server, print server, domain server, internet server, intranet server and other variants such as secondary server, host server, distributed server and the like. The server may include one or more of memories, processors, computer readable media, storage media, ports (physical and virtual), communication devices, and interfaces capable of accessing other servers, clients, machines, and devices through a wired or a wireless medium, and the like. The methods, programs or codes as described herein and elsewhere may be executed by the server. In addition, other devices required for execution of methods as described in this application may be considered as a part of the infrastructure associated with the server.

The server may provide an interface to other devices including, without limitation, clients, other servers, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

If the Subject Methods and Systems are embodied in a software program, the software program may be associated with a client that may include a file client, print client, domain client, internet client, intranet client and other variants such as secondary client, host client, distributed client and the like. The client may include one or more of memories, processors, computer readable media, storage media, ports (physical and virtual), communication devices, and interfaces capable of accessing other clients, servers, machines, and devices through a wired or a wireless medium, and the like. The methods, programs or codes as described herein and elsewhere may be executed by the client. In addition, other devices required for execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of program across the network. The networking of some or all of these devices may facilitate parallel processing of a program or method at one or more location without deviating from the scope of the invention. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The Subject Methods and Systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements.

The methods, program codes, and instructions pertaining to the Subject Methods and Systems described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, EVDO, mesh, or other networks types.

The methods, program codes, and instructions pertaining to the Subject Methods and Systems described herein and elsewhere may be implemented on or through mobile devices. The mobile devices may include navigation devices, cell phones, mobile phones, mobile personal digital assistants, laptops, palmtops, netbooks, pagers, electronic books readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer to peer network, mesh network, or other communications network. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions pertaining to the Subject Methods and Systems may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g. USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The Subject Methods and Systems described herein may transform physical and/or or intangible items from one state to another. The methods and systems described herein may also transform data representing physical and/or intangible items from one state to another.

The elements described and depicted herein and the functions thereof may be implemented on machines through computer executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipments, servers, routers and the like. Furthermore, the elements depicted in the flow chart and block diagrams or any other logical component may be implemented on a machine capable of executing program instructions. Thus, while the foregoing descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied, and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The Subject Methods and Systems, and steps associated therewith, may be realized in hardware, software or any combination of hardware and software suitable for a particular application. The hardware may include a general purpose computer and/or dedicated computing device or specific computing device or particular aspect or component of a specific computing device. The processes may be realized in one or more microprocessors, microcontrollers, embedded microcontrollers, programmable digital signal processors or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as a computer executable code capable of being executed on a machine readable medium.

The computer executable code may be created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, each method described above in connection with the Subject Systems and Methods and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

All documents referenced herein are hereby incorporated by reference.

What is claimed is:

1. A method to detect parameters inside of a lumen comprising:
    inserting an inflatable body into said lumen, said inflatable body having a stretchable surface and a stretchable electronic circuit affixed thereto, said stretchable surface having soft or elastic properties enabling the stretchable surface to be made longer or wider without tearing or breaking, said stretchable electronic circuit being embedded in or affixed to the stretchable surface, the stretchable electronic circuit comprising:
        a plurality of discrete operative devices arranged as device islands on the stretchable surface, the plurality of discrete operative devices including at least one discrete operative device and at least one other discrete operative device; and
        a plurality of stretchable interconnects embedded in or affixed to the stretchable surface to electrically interconnect at least some of the plurality of discrete operative devices, wherein at least one stretchable interconnect of the plurality of stretchable interconnects is directly attached to the at least one discrete operative device and to the at least one other discrete operative device to directly electrically interconnect the at least one discrete operative device to the at least one other discrete operative device;
    inflating the inserted inflatable body to contact the at least one discrete operative device, the at least one other discrete operative device, or a combination thereof to said lumen; and
    measuring a parameter of said lumen in response to the contact.

2. The method of claim 1, further comprising providing a therapy to the lumen based on said measured parameter.

3. The method of claim 1, further comprising generating a graphical output based on said measured parameter.

4. The method of claim 3, wherein the graphical output is a map of the lumen.

5. The method of claim 1, wherein the at least one discrete operative device and the at least one other discrete operative device detect data related to the lumen.

6. The method of claim 5, wherein said data is related to electrical conductivity of plaque inside of the lumen.

7. The method of claim 5, wherein said data is related to pH.

8. The method of claim 5, wherein said data is related to enzymatic activity.

9. The method of claim 5, wherein said data is related to chemical activity.

10. The method of claim 5, further comprising continuously generating said data from the at least one discrete operative device and the at least one other discrete operative device.

11. The method of claim 10, further comprising continuously recording said data generated by the at least one discrete operative device and the at least one other discrete operative device.

12. The method of claim 1, wherein each stretchable interconnect of the plurality of stretchable interconnects is directly attached to respective discrete operative devices of the plurality of discrete operative devices to directly electrically interconnect the plurality of discrete operative devices.

13. The method of claim 2, wherein at least one discrete operative device of the plurality of discrete operative devices comprises a drug delivery polymer comprising a drug.

14. The method of claim 13, further comprising activating the at least one discrete operative device comprising the drug delivery polymer to deliver the drug and provide the therapy to the lumen.

15. The method of claim 14, wherein the drug is an anti-inflammatory drug.

16. The method of claim 1, wherein the measured parameter is temperature data.

17. The method of claim 16, further comprising:
    receiving, at a processor, the temperature data; and
    generating, by the processor, a spatial temperature map of the lumen based on the temperature data.

18. The method of claim 17, further comprising:
    causing, by the processor, an outputting of the temperature map to a display associated with the inflatable body.

19. The method of claim 1, wherein the plurality of discrete operative devices includes an amplifier, a semiconductor structure, a transducer, a photodetector, an ultrasound emitter, a light emitting device, a capacitance sensor, a piezo-electric sensor, a temperature sensor, or a combination thereof.

20. The method of claim 1, wherein the inflatable body is expandable.

21. The method of claim 1, wherein the plurality of discrete operative devices include a plurality of temperature sensors, the method further comprising:
    taking a plurality of temperature measurements via the plurality of temperature sensors at multiple contact points on the lumen; and
    processing the plurality of temperature measurements to produce a spatial temperature map of the lumen, the spatial temperature map indicating plaque on the lumen.

22. The method of claim 21, further comprising:
    determining a plaque type, a location of the plaque, or a combination thereof based on the spatial temperature map.

23. The method of claim 22, further comprising:
    activating one or more drug-delivery devices of the plurality of discrete operative devices to release one or more chemical agents in response to the determined plaque type, the location of the plaque, or a combination thereof.

24. The method of claim 23, wherein a subset of the one or more drug-delivery devices are activated, the subset corresponding to the location of the plaque.

25. The method of claim 23, wherein the one or more chemical agents include one or more anti-inflammatory drugs, one or more drug delivery polymers, or a combination thereof.

26. The method of claim 25, wherein the plurality of discrete operative devices include a plurality of light emitting devices, the method further comprising:
 emitting light from the plurality of light emitting devices to activate the one or more released drug delivery polymers.

27. The method of claim 1, further comprising:
 generating a graphical tactile image map of surface contours of the lumen based on the measured parameter to detect plaque within the lumen.

28. The method of claim 27, wherein the at least one discrete operative device and the at least one other discrete operative device are a pressure sensors, and the measured parameter is a pressure measurement.

29. The method of claim 6, further comprising determining whether the plaque inside the lumen is vulnerable based on the data.

\* \* \* \* \*